(12) United States Patent
Takamoto et al.

(10) Patent No.: US 9,003,865 B2
(45) Date of Patent: Apr. 14, 2015

(54) IN-OIL GAS CONCENTRATION MEASURING SYSTEM AND IN-OIL GAS CONCENTRATION MEASURING METHOD USING SAME SYSTEM

(75) Inventors: Kiyoshi Takamoto, Osaka (JP); Yoshiyuki Oura, Osaka (JP)

(73) Assignee: Kanden Engineering Corporation, Osaka-shi, Osaka (JP)

( * ) Notice: Subject to any disclaimer, the term of this patent is extended or adjusted under 35 U.S.C. 154(b) by 389 days.

(21) Appl. No.: 13/514,359

(22) PCT Filed: Dec. 10, 2009

(86) PCT No.: PCT/JP2009/070704
§ 371 (c)(1),
(2), (4) Date: Aug. 7, 2012

(87) PCT Pub. No.: WO2011/070669
PCT Pub. Date: Jun. 16, 2011

(65) Prior Publication Data
US 2012/0304734 A1    Dec. 6, 2012

(51) Int. Cl.
*G01N 33/28*    (2006.01)

(52) U.S. Cl.
CPC .................................. *G01N 33/2841* (2013.01)

(58) Field of Classification Search
CPC ...... G01N 33/2841; H01F 27/12; H02H 5/06; F01M 11/12; F01M 2250/60
See application file for complete search history.

(56) References Cited

U.S. PATENT DOCUMENTS 3,844,160 A * 10/1974 Yamaoka ..................... 73/19.11
4,112,737 A * 9/1978 Morgan ........................ 73/19.02
4,236,404 A * 12/1980 Ketchum et al. ............. 73/19.02
4,402,211 A * 9/1983 Sugawara et al. ............ 73/19.11
4,437,082 A * 3/1984 Walsh et al. .................... 336/58
4,444,040 A * 4/1984 Sakai et al. ................... 73/19.02

(Continued)

FOREIGN PATENT DOCUMENTS

DE    19833601 C1 * 12/1999    ............... G10N 7/10
EP    1950774 A2 * 7/2008

(Continued)

OTHER PUBLICATIONS

Yoshiyuki Oura et al., "Precision improvement for dissolved gas analysis "Jun. 12, 2009, pp. 19-23, 29th Meeting for reading research papers in subcommittee of isolation oil.

*Primary Examiner* — David A Rogers

(74) *Attorney, Agent, or Firm* — Kratz, Quintos & Hanson, LLP

(57) ABSTRACT

An in-oil gas concentration measuring system comprises: gas extracting which extracts an in-oil gas from an insulating oil sample; component detecting which detects gas components of the in-oil gas extracted by the gas extracting; extracted-gas concentration calculating which calculates, on the basis of data detected by the component detecting, extracted-gas concentrations of the gas components being detected; extracted-gas concentration storing which stores information on the extracted-gas concentrations calculated by the extracted-gas concentration calculating as a result of two or more extractions performed by the gas extracting, the information being stored in each of the extractions; and in-oil gas concentration calculating which calculates in-oil gas concentrations of the gas components on the basis of the extracted-gas concentrations thus stored in the extracted-gas concentration storing.

6 Claims, 5 Drawing Sheets

(56) References Cited

U.S. PATENT DOCUMENTS

| | | | |
|---|---|---|---|
| 4,502,320 A * | 3/1985 | Sakai et al. | 73/19.1 |
| 4,763,514 A * | 8/1988 | Naito et al. | 73/19.11 |
| 4,890,478 A * | 1/1990 | Claiborne et al. | 73/19.11 |
| 5,062,292 A * | 11/1991 | Kanba et al. | 73/19.01 |
| 5,243,848 A * | 9/1993 | Cox et al. | 73/19.05 |
| 5,258,310 A * | 11/1993 | Abe et al. | 436/60 |
| 5,339,672 A * | 8/1994 | Spicar | 73/19.1 |
| 5,400,641 A * | 3/1995 | Slemon et al. | 73/19.01 |
| 6,037,592 A * | 3/2000 | Sunshine et al. | 250/343 |
| 6,289,716 B1 * | 9/2001 | Lindgren | 73/19.1 |
| 6,526,805 B1 * | 3/2003 | Babes-Dornea et al. | 73/19.12 |
| 7,367,217 B2 * | 5/2008 | Stokes et al. | 73/31.06 |
| 7,474,186 B2 * | 1/2009 | Altmann | 336/55 |
| 8,241,916 B2 * | 8/2012 | Toyama et al. | 436/120 |
| 8,423,301 B2 * | 4/2013 | Kato et al. | 702/34 |
| 2003/0172716 A1 * | 9/2003 | Braesel et al. | 73/19.1 |
| 2007/0144236 A1 * | 6/2007 | Stokes et al. | 73/19.11 |
| 2010/0192673 A1 * | 8/2010 | Toyama et al. | 73/23.37 |
| 2011/0175623 A1 * | 7/2011 | Shrinet et al. | 324/537 |
| 2011/0246088 A1 * | 10/2011 | Santos | 702/24 |
| 2013/0247647 A1 * | 9/2013 | Mahoney et al. | 73/19.11 |

FOREIGN PATENT DOCUMENTS

| | | | | |
|---|---|---|---|---|
| JP | 62261958 A | | 11/1987 | |
| JP | 03096829 A | * | 4/1991 | G01N 1/22 |
| JP | 05164754 A | * | 6/1993 | G01N 33/26 |
| JP | 05243053 A | * | 9/1993 | H01F 27/00 |
| JP | 09325138 A | * | 12/1997 | G01N 30/04 |
| JP | 2000241401 A | | 9/2000 | |
| JP | 2003098165 A | | 4/2003 | |
| JP | 2007234687 A | * | 9/2007 | |
| JP | 2007309770 A | * | 11/2007 | |
| JP | 113514359 U | | 8/2012 | |
| WO | WO 2010109474 A1 | * | 9/2010 | |

* cited by examiner

IN-OIL GAS CONCENTRATION MEASURING SYSTEM AND IN-OIL GAS CONCENTRATION MEASURING METHOD USING SAME SYSTEM

TECHNICAL FIELD

The present invention relates to a system for measuring the concentration of an in-oil gas and an in-oil gas measuring method using the same system.

BACKGROUND ART

As a method for detecting faults in an electrical apparatus such as a transformer at an early stage, there has been conventionally known a method for measuring gas components dissolved in an insulating oil (also referred to as "in-oil gas") inside an electrical apparatus. According to this method, it is possible to determine as to whether or not there are any faults in a transformer by measuring typical decomposition gas components (in-oil gas) that are generated when the transformer is in a fault condition, for example, such as local overheating or discharge, and dissolved in an insulating oil, thereby preventing a serious accident. Therefore, this method has been widely utilized for prevention of accidents and maintenance of transformers.

Generally, an analysis of gas components dissolved in an insulating oil in a transformer is carried out in such a manner that a plurality of dissolved gas components (in-oil gas) are extracted to a gas phase part, and the extracted gas components are detected and the concentrations thereof are measured using a gas chromatograph, a gas sensor, or the like (See Patent Documents 1 and 2, for example).

Examples of a method for extracting an in-oil gas to a gas phase part include a replacement extraction method in which an inert gas is injected into an insulating oil as a sample (a sample oil), and an in-oil gas is replaced with the inert gas to thereby extract the in-oil gas, a vacuum extraction method in which a vacuum gas phase part is provided above an insulating oil which is put in an extraction container, and an in-oil gas is extracted to the gas phase part, and an equilibrium extraction method in which a sample oil is encapsulated in a vial container and the like so as to have a gas phase part therein and the vial container is shaken to thereby extract an in-oil gas to the gas phase part by gas-liquid equilibrium.

The replacement extraction method includes a stripping method in which a carrier gas of a gas chromatograph is injected into a sample oil and an extracted in-oil gas is directly introduced into the gas chromatograph, a bubbling method in which a sample oil is bubbled with an inert gas and an extracted in-oil gas is collected in a gas reservoir, and the like.

In the stripping method, an in-oil gas is extracted by using an extractor as shown in FIG. 1, for example. A brief description will be made based on FIG. 1. An insulating oil sample which has been taken in a syringe 1 is injected into an extractor 4 through a sample inlet 3. A carrier gas is then injected through a gas passage 5 into the insulating oil sample 2 which has been injected into the extractor 4 to thereby extract an in-oil gas. The gas which has been extracted (the extracted gas) flows into a gas chromatograph 9 together with the carrier gas through a branch pipe 6 which is provided in an upper part of the extractor 4, a joint 7 and an oil trap 8, and a measurement and an analysis of the extracted gas are then performed in the chromatograph 9.

By the way, when an in-oil gas analysis is carried out using the above-described various methods which have been conventionally performed, there has been widely used a method in which, in order to obtain the in-oil gas concentration in an insulating oil which is an object to be measured (which can be referred to as "a real sample") from a result of a measurement measured by using a gas chromatograph and the like, the in-oil gas concentration in the sample is obtained by the comparison between measurement data of a gas in oil standards in which a known target gas is dissolved and measurement data of the real sample. That is, at first, a target gas the volume of which has been accurately measured is dissolved in an unused insulating oil the mass and the volume of which have been accurately measured after removing a dissolved gas therefrom to thereby prepare a gas in oil standards whose in-oil gas concentration is known. Then, an extraction is performed on the gas in oil standards in the same condition as in a measurement of the real sample. An extraction rate of an extractor to be used for the measurement is calculated from the extracted-gas concentration. Then, when an in-oil gas concentration in the real sample is calculated from a measurement result of the real sample, the in-oil gas concentration in the real sample is corrected with the extraction rate which has been obtained in advance by using the gas in oil standards to thereby calculate the in-oil gas concentration in the real sample.

However, there have been problems in that the preparation of a gas in oil standards as described above has low working efficiency, needs skilled steps, and the like. In order to solve such problems, in Patent Document 3, there has been proposed an apparatus in which the efficiency in agitating an injected standard gas is improved by using a special syringe which is provided with a gas reservoir for the standard gas and a dissolution rate of the standard gas into an insulating oil is therefore increased, thereby improving the working efficiency at the time of preparing a gas in oil standards, for example.

Although the use of the apparatus described in Patent Document 3 could lead to some improvement in the above-described problems, it is still necessary to prepare a gas in oil standards. Therefore, cumbersome and skilled steps are still needed. Further, there is a problem in that an error caused by handling at the time of preparing a gas in oil standards is unavoidable. In addition, there is also another problem in that it is extremely difficult to verify the accuracy of the prepared gas in oil standards.

In particular, when an insulating oil with high viscosity (high-viscosity oil) is used, it is difficult to transfer a sample oil, from which a dissolved gas has been removed, into a syringe. In addition, agitation is difficult to be performed when the dissolved gas is removed from the sample oil and when a target gas is dissolved in the sample oil. Therefore, it is difficult to prepare a gas in oil standards. Further, the conventional extraction method has a low extraction rate and insufficient accuracy. Accordingly, a method of analysis has not yet been established under the present circumstances.

CITATION LIST

Patent Literatures

Patent Document 1: JP-A No. 2000-241401
Patent Document 2: JP-A No. 2000-275150
Patent Document 3: JP-A No. 2003-98165

SUMMARY OF INVENTION

Technical Problem

In view of the above-described problems, it is an object of the present invention to provide an in-oil gas concentration measuring system which is capable of accurately measuring the concentrations of decomposition gas components (in-oil gas) which are dissolved in an insulating oil without using a gas in oil standards which needs cumbersome and skilled steps to be prepared, and also provide an in-oil gas concentration measuring method using the same system.

Solution to Problem

After an intensive investigation to solve the above problems, the inventors of the present invention et al. have found that it becomes possible to measure the in-oil gas concentration with high accuracy without using a gas in oil standards by performing two or more extractions of in-oil gas from an insulating oil sample and using measurement results thereof, and therefore have achieved the present invention.

Thus, a first aspect of the present invention is directed to an in-oil gas concentration measuring system which includes gas extracting means for extracting an in-oil gas from an insulating oil sample; component detecting means for detecting gas components of the in-oil gas extracted by the gas extracting means; extracted-gas concentration calculating means for calculating extracted-gas concentrations of the gas components being detected, based on data detected by the component detecting means; extracted-gas concentration storing means for storing information on the extracted-gas concentrations calculated by the extracted-gas concentration calculating means as a result of two or more extractions performed by the gas extracting means, the information being stored in each of the extractions; and in-oil gas concentration calculating means for calculating in-oil gas concentrations of the gas components based on the extracted-gas concentrations stored in the extracted-gas concentration storing means, wherein the in-oil gas concentration calculating means calculates an in-oil gas concentration (Q) by using the following equation (1), where Q denotes an in-oil gas concentration to be calculated, R denotes an extraction rate of an in-oil gas, and $X_n$ denotes an extracted-gas concentration at n-th time extracted from the extracted-gas concentration storing means.

$$X_n = R\left(Q - \sum_{k=1}^{n} X_{k-1}\right)(n = 1, 2, \text{ and so on}, X_0 = 0) \quad (1)$$

In the present invention, the component detecting means may be provided with flow line switching means for controlling opening and closing of a gas flow line for supplying the in-oil gas extracted by the gas extracting means to the component detecting means.

Further, in the present invention, the gas extracting means may be provided with discharge preventing means for the insulating oil sample.

Furthermore, in the present invention, the gas extracting means may be composed of an in-oil gas analyzing apparatus having measuring means for measuring the insulating oil sample.

A second aspect of the present invention is directed to an in-oil gas concentration measuring method which includes providing gas extracting means for extracting an in-oil gas from an insulating oil sample, component detecting means for detecting gas components of the in-oil gas extracted by the gas extracting means, extracted-gas concentration calculating means for calculating extracted-gas concentrations of the gas components being detected, based on data detected by the component detecting means, extracted-gas concentration storing means for storing information on the extracted-gas concentrations calculated by the extracted-gas concentration calculating means, and in-oil gas concentration calculating means for calculating in-oil gas concentrations of the gas components based on the extracted-gas concentrations stored in the extracted-gas concentration storing means; performing a sequence of steps twice or more, the steps including extracting an in-oil gas by the gas extracting means, detecting gas components of the in-oil gas by the component detecting means, calculating gas concentrations of the gas components being detected, by the extracted-gas concentration calculating means, and storing information on the extracted-gas concentrations by the extracted-gas concentration storing means; and calculating an in-oil gas concentration (Q) by the in-oil gas concentration calculating means by using the following equation (1), where Q denotes an in-oil gas concentration to be calculated, R denotes an extraction rate of an in-oil gas, and $X_n$ denotes an extracted-gas concentration at n-th time extracted from the extracted-gas concentration storing means.

$$X_n = R\left(Q - \sum_{k=1}^{n} X_{k-1}\right)(n = 1, 2, \text{ and so on}, X_0 = 0) \quad (1)$$

Advantageous Effects of Invention

According to the present invention, the concentrations of decomposition gas components (in-oil gas) which are dissolved in an insulating oil can be measured with high accuracy without using a gas in oil standards which needs cumbersome and skilled steps to be prepared.

DESCRIPTION OF EMBODIMENT

Figure 1:
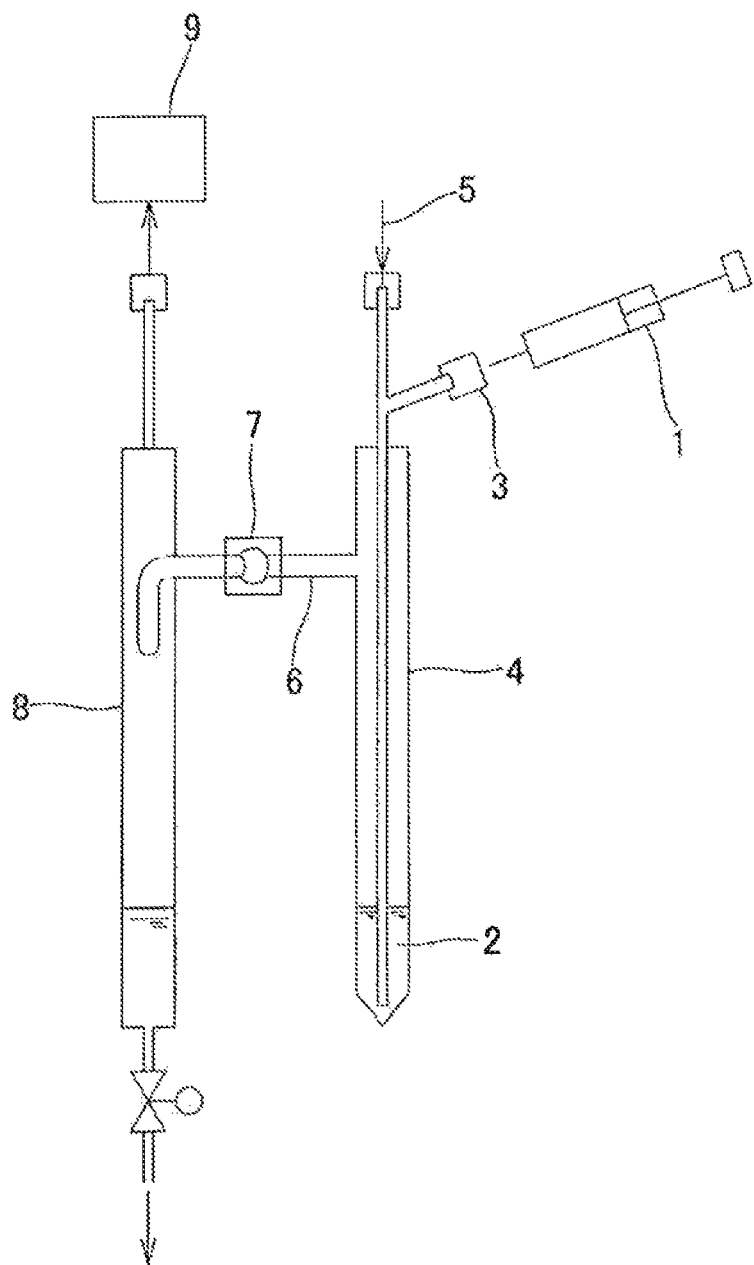
FIG. 1 is a schematic view showing an example of a conventional extractor.

Hereinafter, an embodiment of the present invention will be described based on the appended drawings. In an embodiment shown in FIG. 2, an in-oil gas concentration measuring system 10 of the present invention is schematically shown. In the in-oil gas concentration measuring system 10, in order to measure a plurality of gas components which are dissolved in an insulating oil inside an electrical apparatus such as a transformer, two or more extractions of an in-oil gas are performed with respect to a single insulating oil sample taken from the transformer and the like to thereby measure in-oil gas concentrations. Further, the in-oil gas concentration measuring system 10 is provided with at least gas extracting means 11 which extracts an in-oil gas from an insulating oil sample, component detecting means 12 which detects components of the in-oil gas which has been extracted, and an arithmetic unit 22 which calculates the in-oil gas concentration by quantifying a single gas component detected by the component detecting means 12.

The gas extracting means 11 performs a step for extracting an in-oil gas from an insulating oil sample which has been taken from an electrical apparatus such as a transformer. The gas extracting means 11 is composed of an in-oil gas extracting apparatus which includes an extractor 13 which extracts an in-oil gas from an insulating oil sample taken from various electrical apparatuses, an electric six-direction switching cock (a) 14 which switches flow circuits of gas and the insulating oil sample into or out of the extractor, a sample holding container 15 for temporarily storing the insulating oil sample, measuring means (measuring tube) 16 for measuring the insulating oil sample to be introduced into the extractor, and a feed pump 17 for introducing the insulating oil sample into the measuring tube 16.

The extractor 13 is a generally cylindrical hollow container which is formed from an oil-proof metal, an oil-proof glass, an oil-proof resin or the like and is capable of maintaining a sealed state thereof. A passage P1 is provided in a top surface of the extractor 13. One end of the passage P1 is connected to a port A of the electric six-direction switching cock (a) 14 which is provided with ports A to F, and the other end of the passage P1 extends down to near a bottom of the extractor through the inside thereof. Further, a passage P2 and a passage P3 are provided in an upper part of a side surface of the extractor. The passage P2 and the passage P3 are respectively connected to a port L and a port J of an electric six-direction switching cock (b) 23 which is provided with ports G to L and will be described later. Further, the passage P3 branches off from the passage P1.

Figure 2:
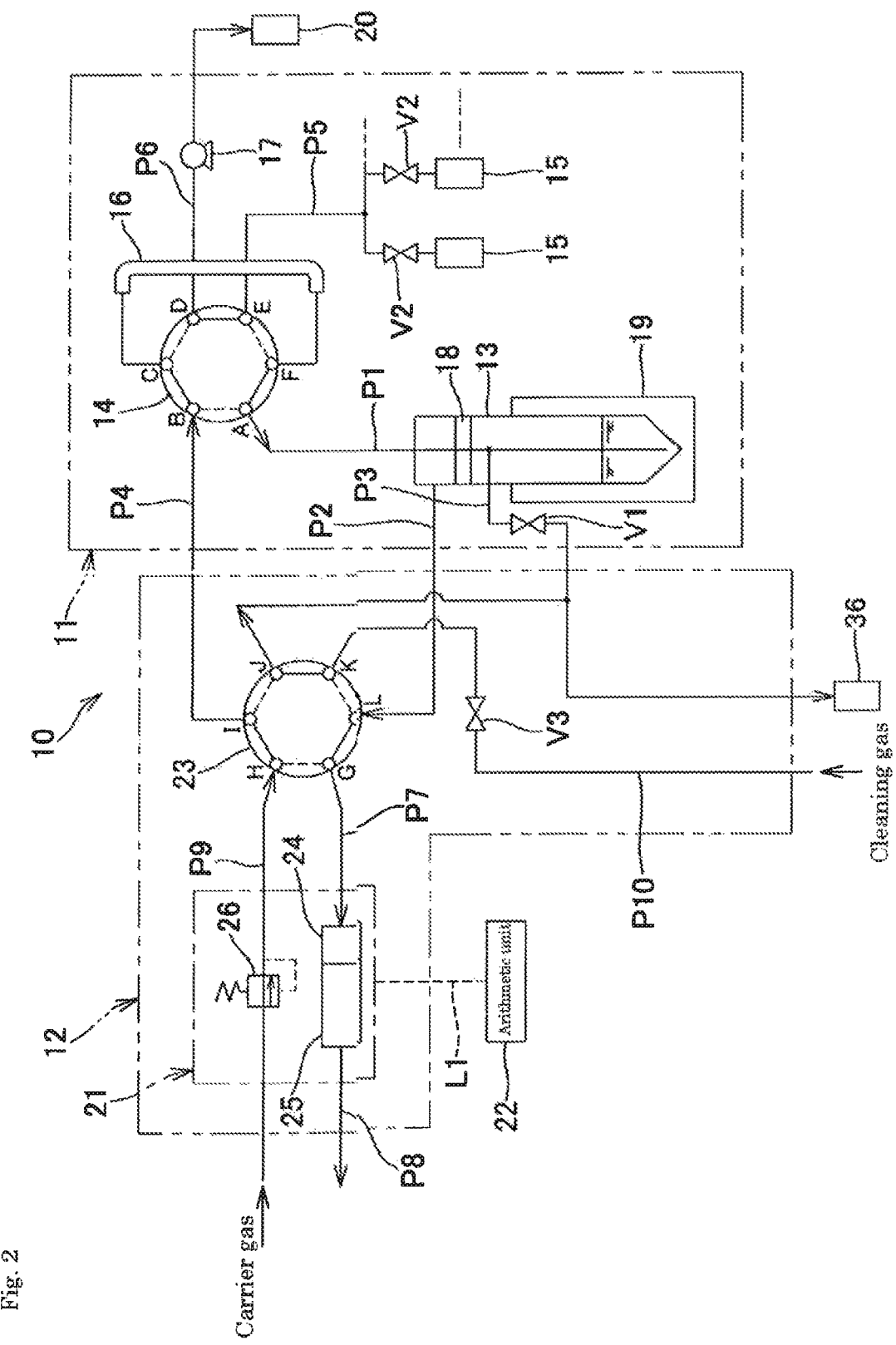
FIG. 2 is a schematic view showing an example of a in-oil gas concentration measuring system of the present invention.

In addition, although the passage P3 branches off from the passage P1 at an upper part of the inside of the extractor 13 in FIG. 2, the passage P3 may also branch off from the passage P1 outside of the extractor 13. Further, a solenoid valve V1 which switches the communication between the inside of the extractor 13 and the port J is provided in the passage P3.

Further, it is preferred that discharge preventing means 18 for preventing discharge to the outside of an extractor system be provided in the upper part of the extractor 13 in order to prevent the insulating oil sample which has been introduced into the inside of the extractor 13 from being discharged to the outside of the extractor 13 through the passage P2 and the like when the in-oil gas is extracted. As will be described later, when a gas for extracting an in-oil gas (hereinafter, which can also be referred to as a carrier gas) is introduced into the extractor 13, it often happens that oil films and oil bubbles come out of the insulating oil sample and are then discharged together with the gas to the outside of the system of the extractor 13 through the passage P2 and the like. In the present invention, two or more extraction treatments are performed with respect to a single insulating oil sample which has been introduced into the extractor 13 and the in-oil gas concentration and the like are calculated by using the above equation (1), as will be described later. Therefore, if the insulating oil sample is discharged to the outside of the extractor 13, the calculation cannot be performed. As for the configuration of the discharge preventing means 18 for preventing discharge to the outside of the extractor system, any preventing means can be used as long as it is capable of destroying oil films and oil bubbles which have come out of the insulating oil as well as allowing gas to pass therethrough. For example, a netlike or spiral filter which is made of an oil-proof material (an oil-proof metal, for example) can be used. Further, the discharge preventing means 18 may also be provided with a needle-like structure for destroying the oil films and the oil bubbles. Furthermore, it is also possible to make the height of the extractor 13 further taller in order to extend the flowing distance of the oil films and the oil bubbles from a surface of the insulating oil sample to the passage P2 and the like.

In addition, in FIG. 2, heating means 19 is provided around the side surface and the bottom surface of the extractor 13 in order to lower the viscosity of the insulating oil sample so that the surface area of an air bubble of the carrier gas in the sample becomes larger and an extraction rate of the in-oil gas is thereby increased. Therefore, the heating means 19 is particularly effective for the case where the insulating oil sample has high viscosity. A temperature condition at the time of using the heating means is not particularly limited as long as an extraction rate (especially, a calculated value in the first extraction) in an insulating oil sample can fall within a predetermined range which will be described later. However, in order to prevent the generation of additional decomposition gases, the temperature of the insulating oil sample (the extraction temperature) is preferably in the range of 40 to 100° C. Specifically, known heating means such as a heater can be used as the heating means 19. Further, it is preferred to use heating means which is capable of controlling temperature with a thermometer (not shown in the drawing) placed inside the extractor.

The electric six-direction switching cock (a) 14 is provided with the ports A to F. The port A is connected to the extractor 13, the port B is connected to the electric six-direction switching cock (b) 23, the port E is connected to the sample holding container 15, and the ports C and F are connected to the measuring tube 16. The electric six-direction switching cock (a) 14 has a role in switching a flow line of the carrier gas. That is, when the carrier gas is introduced into the gas extracting means 11 from the component detecting means 12, the electric six-direction switching cock (a) 14 makes a choice as to whether or not the carrier gas is introduced into the extractor 13 by way of the measuring tube 16. Therefore, the electric six-direction switching cock (a) 14 does not control opening and closing of a flow line for supplying the extracted gas to the component detecting means 12.

The sample holding container 15 is used for storing an insulating oil sample which has been taken from a transformer and the like, and is connected to the port E of the electric six-direction switching cock (a) 14 through a passage P5. Further, a solenoid valve V2 which switches the communication between the sample holding container 15 and the electric six-direction switching cock (a) 14 is provided in the passage P5. Furthermore, as shown in FIG. 2, when a plurality of insulating oil samples are measured, it is preferred to prepare a plurality of the sample holding containers 15, and provide a passage which branches off from the passage P5 and a solenoid valve for the respective holding containers 15.

One end of a passage P6 is connected to the port D of the electric six-direction switching cock (a) 14. In addition, the feed pump 17 for introducing the insulating oil sample stored in the sample holding container 15 into the measuring tube 16 is provided in the passage P6. Further, the other end of the passage PC is connected to a waste container 20 into which the insulating oil sample is discharged.

The measuring tube 16 is a tubular member which is impervious to gas and is made of a material such as an oil-proof metal, an oil-proof glass or an oil-proof resin. The measuring tube 16 holds a certain amount of the insulating oil sample in an internal space thereof having a predetermined volume. The insulating oil sample is introduced into the measuring tube 16 from the sample holding container 15 through the electric six-direction switching cock (a) 14 by means of the feed pump 17. The insulating oil sample which has been introduced into the inside of the measuring tube is then introduced into the inside of the extractor 13 to be subjected to a measurement of the in-oil gas concentration.

Further, although the electric six-direction switching cock (a) 14, the measuring tube 16, the sample holding container 15 and the like are used when introducing the insulating oil sample into the extractor 13 in this embodiment, it is also possible to use a syringe as shown in FIG. 1 instead of these members.

The component detecting means 12 is composed of a detecting unit 21 and a flow line switching means 23. In FIG. 2, the flow line switching means 23 is the electric six-direction switching cock (b) which is provided with the ports G to L.

The detecting unit 21 is composed of a separator 24 which separates each of components from the multicomponent in-oil gas which has been extracted in the gas extracting means 11, a component detector 25 which detects each of the separated components of the in-oil gas, and a flow regulating valve 26 which regulates the amount of the carrier gas to be injected.

The separator 24 is not particularly limited to any specific one as long as it can separate a plurality of components contained in the in-oil gas. For example, a separation column which is commonly used in a gas chromatograph can be used. In particular, examples of the separation column include a column that uses activated alumina as a filler, the activated alumina being capable of separating a hydrocarbon contained in the in-oil gas as a component thereof.

One end of the separator 24 is connected to the port G of the electric six-direction switching cock (19) 23 through a passage P7. On the other hand, the other end of the separator 24 is connected to the component detector 25. Further, when carbon monoxide or carbon dioxide is contained in the in-oil gas as a component thereof, a methanizer which is used for a methanation of these components may be provided in the separator 24. In this case, a commercially available methanizer can be used.

The component detector 25 detects each of the gas components which have been separated in the separator 24. As the component detector 25, it is possible to utilize various detectors used in a gas chromatograph and the like, such as a flame ionization detector (FID), a thermal conductivity detector (TCD), and a photo ionization detector (PID). The component detector 25 is provided with a passage P8 through which the detected gas components and the like are discharged to the outside (it is preferred to collect and treat these components).

A detected signal (detected data) of the respective single gas components detected by the component detector 25 is sent to an arithmetic unit 22, which will be described later, through a line L1.

In order to stimulate performance of the separator 24 and improve detection sensitivity of the component detector 25, the separator 24 and the component detector 25 are heated up by using heating means (not shown in the drawing) such as a heater so as to be maintained at a predetermined temperature in the range of 40 to 100° C.

The flow regulating valve 26 is used for regulating an injection amount of the carrier gas, that is, regulating a flow rate and a flow time of the carrier gas when the extraction is performed in the extractor 13. In the prevent invention, two or more extractions of an in-oil gas are performed with respect to a single sample, as will be described later. Therefore, it is preferred that the generation of oil films and oil bubbles as described above can be suppressed and the extraction amount of the in-oil gas in each of the extractions can fall within a detectable range for the component detector 25. On the other hand, a measurement time is preferably as short as possible. Based on this standpoint, the flow rate of the carrier gas is preferably regulated so as to be in the range of 30 to 50 mL/min in the present invention. Further, the flow time of the carrier gas at the time of the extraction (the extraction time) is preferably in the range of 30 to 90 seconds.

Further, as for the carrier gas to be used, it is preferred to use a gas that has no influence on the separator 24, the component detector 25, and an insulating oil sample. An inert gas such as nitrogen, helium, or argon is used.

The detecting unit 21 as described above can be composed of a known apparatus such as a gas chromatograph, or a part of the functions of the same apparatus.

The flow line switching means 23 of the component detecting means 12 has a role in switching flow lines of the carrier gas, the extracted in-oil gas, a cleaning gas for cleaning the inside of the extractor 13, and the insulating oil sample removed from the extractor 13. In FIG. 2, the flow line switching means 23 is shown as the electric six-direction switching cock (b) 23 provided with the ports G to L. The port G is connected to the separator 24 through the passage P7. The port H is connected to a carrier gas supply source (not shown in the drawing) through a passage P9. The port I is connected to the port B of the electric six-direction switching cock (a) 14 through a passage P4. The port J is connected to the passage P3 to thereby communicate with the inside of the extractor 13 and also connected to the waste container 36 for housing the insulating oil sample after the measurement. The port K is connected to the passage P10 to thereby communicate with a gas source of a cleaning gas for discharging the insulating oil sample in the extractor 13 and then cleaning the inside of the extractor 13. Further, a solenoid valve V3 which controls the introduction of the cleaning gas is provided in the passage P10. Further, the port L is connected to the passage P2 to thereby communicate with the inside of the extractor 13.

The flow line switching means 23 as described above has a role mainly in controlling opening and closing of a gas flow line for supplying the in-oil gas which has been extracted by the gas extracting means 11 to the component detecting means 12 by controlling the communication between the port H and the port G.

The arithmetic unit 22 calculates the in-oil gas concentration by quantifying the respective single gas components detected by the detecting unit 21 of the component detecting means 12. The arithmetic unit 22 is connected to the detecting unit 21 through the line L1.

Figure 3:
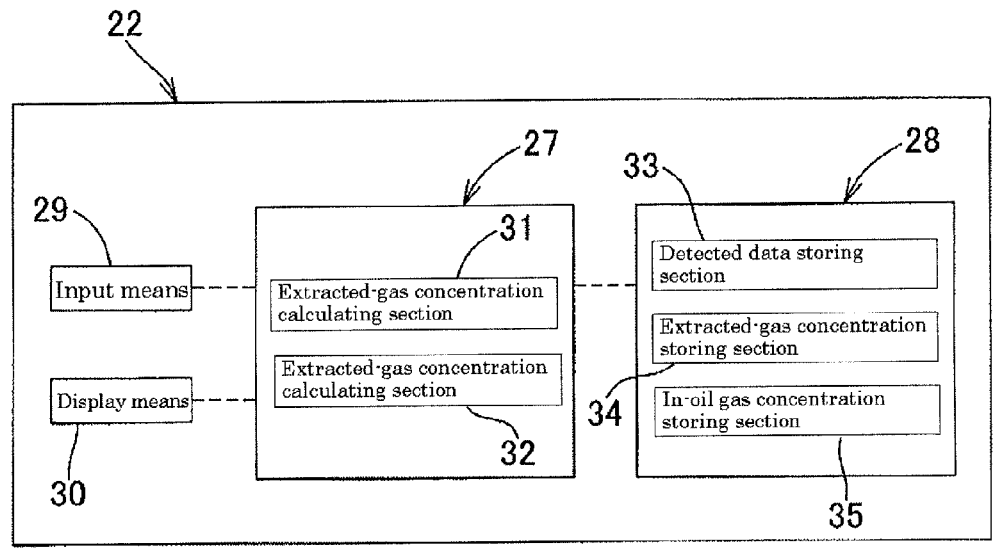
FIG. 3 is a schematic view showing an example of the configuration of a processing unit used in the present invention.

As shown in FIG. 3, the arithmetic unit 22 is a computer which includes a processing unit 27 as a main component. Further, the arithmetic unit 22 includes a storage unit 28, input means 29 such as a mouse and a keyboard, and display means 30 such as a display for outputting a calculation result and the like all of which are connected to the processing unit 27. The processing unit 27 is mainly composed of CPU such as a microprocessor and includes a memory unit (not shown in the drawing) which is composed of RAM and ROM. In the memory unit, a program which defines procedures of various processing operations and processing data are stored.

From a functional point of view, the processing unit 27 includes at least an extracted-gas concentration calculating section 31 as extracted-gas concentration calculating means which calculates extracted-gas concentrations of the gas components which have been detected, based on the data detected by the component detecting means 12 and an in-oil gas concentration calculating section 32 as in-oil gas concentration calculating means which calculates in-oil gas concentrations of the gas components, based on the thus calculated extracted-gas concentrations. These functions are defined by the above-described program.

Further, the storage unit 28 includes at least a detected data storing section 33 which stores the data which has been detected by the component detecting means 12, an extracted-gas concentration storing section 34 which stores information on the extracted-gas concentrations which have been calculated by the extracted-gas concentration calculating section 31, and an in-oil gas concentration storing section 35 which stores the in-oil gas concentrations which have been calculated by the in-oil gas concentration calculating section 32.

The extracted-gas concentration calculating section 31 calculates the concentration of the respective single gas components based on the detected signal of the respective single gas components, the detected signal being detected in the detecting unit 21 and stored in the detected data storing section 33, and stores the thus calculated result on the extracted-gas concentration storing section 34. In this embodiment, information on the concentration of the respective single gas components of the extracted in-oil gas is stored in the extracted-gas concentration storing section 34 in each of the in-oil gas extractions which are performed twice or more by the gas extracting means 11.

The in-oil gas concentration calculating section 32 calculates an in-oil gas concentration (Q), and also calculates an extraction rate (R) of an in-oil gas as needed, by using the above-described equation (1), where Q denotes an in-oil gas concentration to be calculated, R denotes an extraction rate of an in-oil gas, and $X_n$ denotes an extracted-gas concentration at n-th time extracted from the extracted-gas concentration storing section 34.

The equation (1) is based on an empirical equation which is regarded as holding between a gas component contained in an insulating oil and the gas component which has been extracted into the gas phase. Calculation principles of the in-oil gas concentration (Q) and the extraction rate (R) of a certain component will be described taking the case of n=3 as an example. When the first extraction is performed, the relationship of $X_1=RQ$ is satisfied. R and Q are unknown constants. On the other hand, $X_1$ is a calculated value (known) based on the detected data. Further, when the second extraction is performed, since the in-oil gas have already been extracted from the insulating oil in the first extraction, an in-oil gas having a concentration of $(Q-X_1)$ exists in the insulating oil. The concentration in the gas phase at this time is $X_2$, and the relationship of $X_2=R(Q-X_1)$ is satisfied. Based on these two equations, R and Q which are unknown constants are calculated as $R=(X_1-X_2)/X_1$, and $Q=X_1^2/(X_1-X_2)$. In this manner, the concentration (Q) and the extraction rate (R) of the in-oil gas dissolved in the insulating oil sample are calculated.

In addition, when the third extraction is performed for confirming the reliability of the thus calculated value (Q), the relationship of $X_3=H(Q-X_1-X_2)$ is satisfied. Further, based on the two equations of $X_3=R(Q-X_1-X_2)$ and $X_1=RQ$, R is calculated as $R=(X_1-X_3)/(X_1+X_2)$. When an extraction rate which was obtained based on measurement results of the first and second extractions is defined as R1 and an extraction rate which was obtained based on measurement results of the first, second and third extractions is defined as R2, calculating an extraction rate ratio of R1/R2 makes it possible to confirm the reliability of the in-oil gas concentration (Q) of a certain component. In this case, when the extraction rate R1 is equal to or greater than 0.5 and preferably equal to or greater than 0.6, and the extraction rate ratio is in the range of 0.90 to 1.10, preferably in the range of 0.94 to 1.02, and more preferably in the range of 0.97 to 1.02, it can be judged that the calculated in-oil gas concentration (Q) is reliable.

Although the example in the case of n=3 has been described as above, it is also possible to carry out the same calculation based the extractions performed any number of times. Further, the operations of the gas extracting means 11 and the component detecting means 12 can be controlled by using the computer as the arithmetic unit 22. Furthermore, the calculation of the extracted-gas concentration and the calculation of the in-oil gas concentration can also be respectively performed by using different arithmetic units.

The insulating oil that can be measured in the present invention is not particularly limited to any specific one. Therefore, various kinds of insulating oils can be used, such as a JIS Class I oil, a mineral oil, and a vegetable oil. Namely, it is possible to measure not only an insulating oil with low viscosity, but also an insulating oil with high viscosity.

Figure 4:
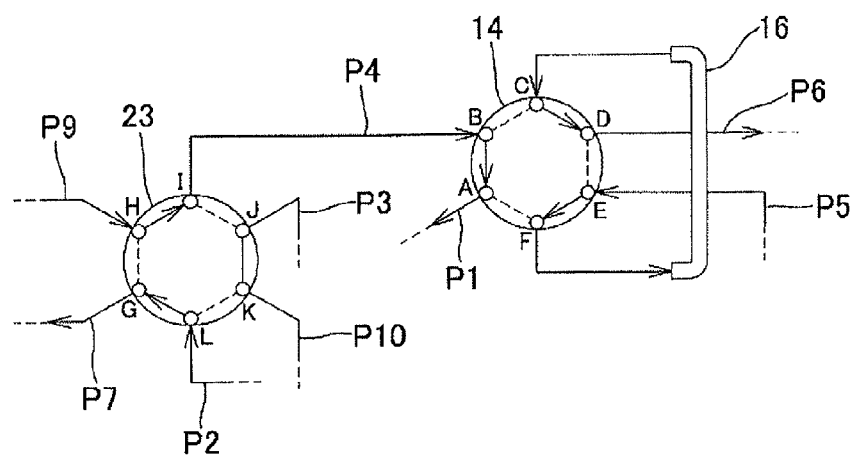
FIG. 4 is a schematic view showing a communication state between ports of each of electric six-direction switching cocks, and passages at the time of measuring an insulating oil sample in an embodiment of the present invention.

Next, a description will be made with regard to an operation of the in-oil gas concentration measuring system in the present embodiment. At first, an insulating oil sample, a carrier gas, and a cleaning gas are prepared. The in-oil gas concentration measuring system 10 is then powered on to thereby activate the arithmetic unit 22, so that the port A communicates with the port B, the port C communicates with the port D, and the port E communicates with the port F in the electric six-direction switching cock (a) 14, and also the port H communicates with the port I, the port J communicates with the port K, and the port L communicates with the port G in the electric six-direction switching cock (b) 23, as shown in FIG. 4. Accordingly, the carrier gas flows through the passage P9, the port H, the port I, the port B, the port A, the passage P1, the extractor 13, the passage P2, the port L, the port G, the separator 24, and the component detector 25 in this order at a regulated flow rate which has been regulated by the flow regulating valve 26, and then flows off to the outside. At the same time, the feed pump 17 is activated, so that the insulating oil sample flows from the sample holding container 15 through the solenoid valve V2 which is being opened, the passage P5, the port E, the port F, the measuring tube 16, the port C, the port D, and the passage P6 in this order. By maintaining this state for a while, the passages are cleaned with the carrier gas, and the inside of the measuring tube 16 is filled with the insulating oil sample. In addition, temperatures of the detecting unit 21 and the heating means 19 for the extractor 13, the heating cans being provided as needed, are each made to be a predetermined temperature. Further, the solenoid valves V1 and V3 are kept closed.

Figure 5:
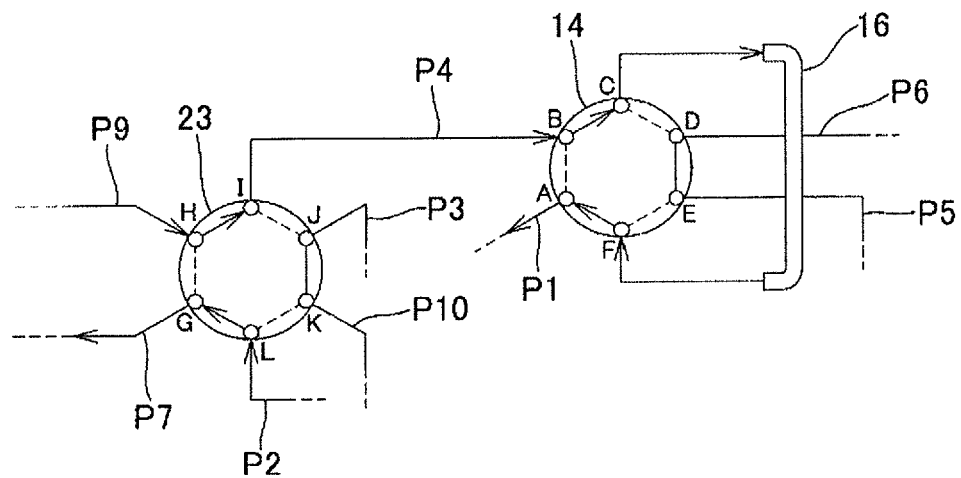
FIG. 5 is a schematic view showing a communication state between the ports of each of the electric six-direction switching cocks, and the passages at the time of performing an extracting operation of in-oil gas in the embodiment of the present invention.

Next, as shown in FIG. 5, the flow lines are switched so that the port B communicates with the port C, the port D communicates with the port E, and the port F communicates with the port A in the electric six-direction switching cock (a) 14 while maintaining the communication state between the ports in the electric six-direction switching cock (b) 23. At or about this time, the feed pump 17 stops working, and the solenoid valve V2 is closed. Accordingly, the carrier gas is introduced into the measuring tube 16. As a result, the insulating oil sample in the measuring tube is sent to the inside of the extractor 13 through the passage P1, and an in-oil gas is extracted from the insulating oil sample. During this time, the extracted in-oil gas passes through the discharge preventing means 18 for preventing discharge to the outside of the system of the extractor 13, and is then introduced into the separator 24 through the passages P2 and P7. On the other hand, the insulating oil sample remains held inside the extractor 13 as described above. In the separator 24, the extracted multicomponent in-oil gas is separated into each of components. The thus separated components are then sequentially introduced into the component detector 25. In the component detector 25, each of the components is detected as a signal corresponding to the concentration thereof. The detected signal (detected data) is sent to the processing unit 22 through the line L1. In the processing unit 22, a concentration of the respective single gas components is calculated based on the detected data (the detected data can be stored in the detected data storing section). Then, information on the extracted-gas concentration of each of the components is stored in the extracted-gas concentration storing section 34 as a first measurement result.

Figure 6:
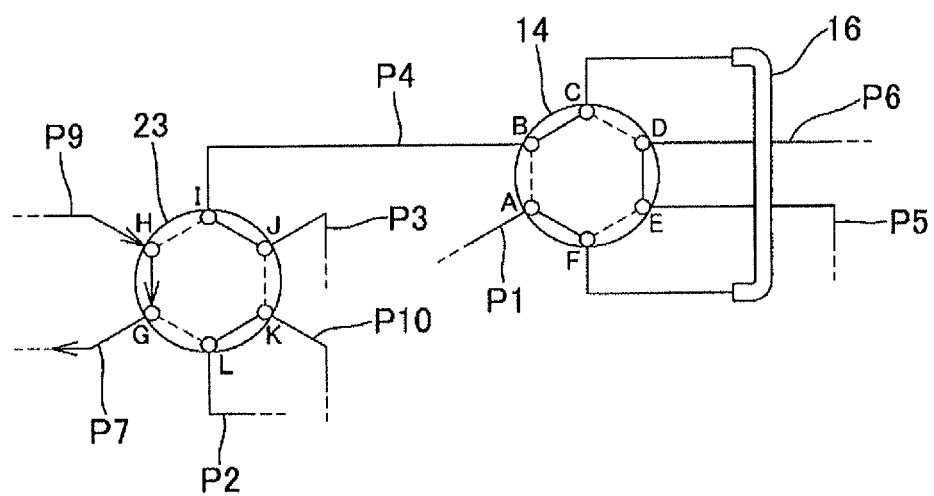
FIG. 6 is a schematic view showing a communication state between the ports of each of the electric six-direction switching cocks, and the passages after the extracting operation of in-oil gas was performed in the embodiment of the present invention.

After a preset time has passed, the flow lines are switched so that the port H communicates with the port G, the port I communicates with the port J, and the port K communicates with the port L in the electric six-direction switching cock (b) 23 while maintaining the communication state between the ports in the electric six-direction switching cock (a) 14 as shown in FIG. 6. Accordingly, the carrier gas is directly introduced into the separator 24 and the component detector 25 through the passage P9, the port H, the port G, and the passage P7 without passing through the extractor 13, and the processes in the component detecting means 12 and the arithmetic unit 22 are being continued. On the other hand, the inside of the extractor 13 is kept in an airtight state.

After the calculated result of the extracted-gas concentration of the respective components of the in-oil gas has been stored in the extracted-gas concentration storing section 34, and the separator 24 and the component detector 25 have become ready for another measurement, the communication state between the ports in each of the electric six-direction switching cock (a) 14 and the electric six-direction switching cock (b) 23 is again switched as shown in FIG. 5, and the second extraction is then performed. Further, after the predetermined time has passed, the communication state between the ports in each of the cocks is again switched as shown in FIG. 6. When the above operation is further repeated once or more, a calculated result of the extracted-gas concentration of the respective components of the in-oil gas is stored in the extracted-gas concentration storing section 34 in each operation.

In this manner, a sequence of steps including the extraction of an in-oil gas by the gas extracting means 11, the detection of components of the in-oil gas by the component detector 25, the calculation of the concentrations of the detected gas components by the extracted-gas concentration calculating means 31, and the storage of information on the extracted-gas concentrations by the extracted-gas concentration storing section 34 is performed twice or more, and the in-oil gas concentration (Q) is calculated by the in-oil gas concentration calculating section 32 by using the above-described equation (1) which is expressed using an extracted-gas concentration of a given gas component, the extracted-gas concentration being extracted from the extracted-gas concentration storing section 34. Further, it is also possible to calculate the extraction rate (R) and thereby calculate the extraction rate ratio in order to confirm the reliability of the measurement as described above.

As described above, the in-oil gas concentration can be measured by using the in-oil gas concentration measuring system of the present invention. In addition, it is also possible to perform the measurement using a plurality of insulating oil samples in the present invention. In such a case, it is necessary to replace an insulating oil sample which has been already measured and is held in the extractor 13 with a new insulating oil sample. Therefore, such an operation will be described below.

Figure 7:
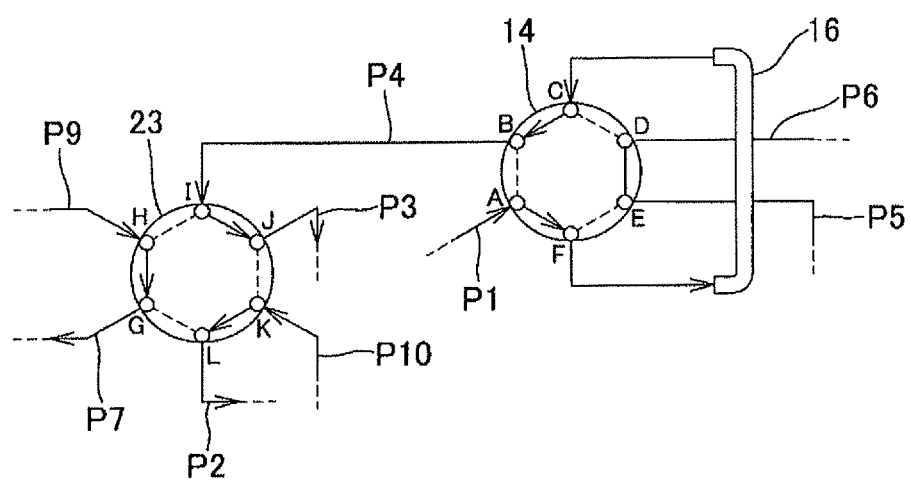
FIG. 7 is a schematic view showing a communication state between the ports of each of the electric six-direction switching cocks, and the passages at the time of discharging the insulating oil sample which has already been measured from an extractor in the embodiment of the present invention.

As described above, when the measurement of the in-oil gas concentration is finished, each of the cocks is in the communication state as shown in FIG. 6. In such a state, the solenoid valves V1 and V3 are opened. A cleaning gas is then introduced into the extractor 13 through the passage P10, the ports K and L of the electric six-direction switching cock (b) 23, and the passage P2 so as to feed the insulating oil sample held in the extractor 13 with pressure, thereby discharging the insulating oil sample into the waste container 36 through the passages P1 and P3 (See FIG. 7). The cleaning gas is then circulated through the passages for a while. After that, the communication state of each of the cocks is changed as shown in FIG. 4. In this state, it is possible to measure the in-oil gas concentration in the same manner as above using another insulating oil sample.

Further, the cleaning gas is not particularly limited to any specific one. A gas that can be used as the above-described carrier gas may be used as the cleaning gas.

Further, the opening and closing of the respective cocks, the opening and closing of the respective solenoid valves, and the temperature regulation of the heating means which is performed as needed may also be carried out by the computer as the arithmetic unit 22 as described above.

EXAMPLES

Next, examples of the above-described embodiment will be described below.

As an insulating oil, a general transformer oil (JIS Class 1 oil, Kinematic viscosity: 8.5 mm$^2$/s at 40° C.) (Table 1), a high-viscosity insulating oil (Kinematic viscosity: 124 mm$^2$/s at 40° C.) (Table 2), and a rapeseed oil (Kinematic viscosity: 35.4 mm$^2$/s at 40° C.) (Table 3) were respectively used in measurements result of which are respectively shown in Tables 1 to 3. In the respective measurements, a gas in oil standards in which typical hydrocarbons contained in these insulating oils ($CH_4$, $C_2H_4$, $C_2H_2$, $C_3H_8$, iso-$C_4H_{10}$) are dissolved was prepared to be used as an insulating oil sample. In the extraction conditions (extraction time and extraction temperature) shown in Tables 1 to 3, the in-oil gas concentration (Q) and the extraction rates (R1 and R2) of the respective components of the insulating oil sample were calculated by using the in-oil gas concentration measuring system of the present invention. The thus calculated values were compared to actual values, and the comparison results will be shown in Tables 1 to 3. Further, in these examples, the calculations were performed using the equation (1) in the case of n=3. In each of Tables 1 to 3, "Error (concentration)" is a ratio of a difference between the adjusted concentration and the calculated concentration (Q) to the adjusted concentration, the ratio being expressed in percentage. Further, "Actual extraction rate" is a ratio of the extracted-gas concentration $X_1$ to the adjusted concentration. Further, "Error (extraction)" is a ratio of a difference between the actual extraction rate and the extraction rate R1 to the actual extraction rate, the ratio being expressed in percentage.

6 Branch pipe
7 Joint
8 Oil trap

TABLE 1

| Component | Extraction condition | | Extracted-gas concentration $X_n$ (μL/L) | | | Adjusted concentration [μL/L] | Calculated concentration [μL/L] | Error (concentration) [%] | Actual extraction rate [—] | Extraction rate R1 [—] | Error (extraction) [%] | Extraction rate R2 [—] | R1/R2 [—] |
|---|---|---|---|---|---|---|---|---|---|---|---|---|---|
| | Time (second) | Temperature (° C.) | 1st time $X_1$ | 2nd time $X_2$ | 3rd time $X_3$ | | | | | | | | |
| $CH_4$ | 45 | 25 | 783 | 149 | 33 | 999 | 973 | −2.6 | 0.790 | 0.811 | −2.7 | 0.806 | 1.006 |
| $C_2H_4$ | 45 | 25 | 737 | 197 | 56 | 995 | 987 | 0.2 | 0.731 | 0.729 | 0.2 | 0.726 | 1.004 |
| $C_2H_2$ | 45 | 25 | 780 | 174 | 49 | 999 | 958 | −4.1 | 0.731 | 0.762 | −4.2 | 0.783 | 1.011 |
| $C_3H_8$ | 90 | 25 | 786 | 170 | 44 | 995 | 1002 | 0.7 | 0.789 | 0.783 | 0.2 | 0.776 | 1.010 |
| iso-$C_4H_{10}$ | 90 | 25 | 596 | 262 | 114 | 1002 | 1064 | 6.1 | 0.585 | 0.560 | 5.8 | 0.562 | 0.398 |

TABLE 2

| Component | Extraction condition | | Extracted-gas concentration $X_n$ (μL/L) | | | Adjusted concentration [μL/L] | Calculated concentration [μL/L] | Error (concentration) [%] | Actual extraction rate [—] | Extraction rate R1 [—] | Error (extraction) [%] | Extraction rate R2 [—] | R1/R2 [—] |
|---|---|---|---|---|---|---|---|---|---|---|---|---|---|
| | Time (second) | Temperature (° C.) | 1st time $X_1$ | 2nd time $X_2$ | 3rd time $X_3$ | | | | | | | | |
| $CH_4$ | 45 | 80 | 736 | 174 | 39 | 999 | 984 | −3.5 | 0.737 | 0.764 | −3.6 | 0.766 | 0.997 |
| $C_2H_4$ | 45 | 80 | 668 | 209 | 46 | 995 | 972 | −2.3 | 0.673 | 0.657 | −2.3 | 0.703 | 0.969 |
| $C_2H_2$ | 45 | 80 | 717 | 193 | 44 | 999 | 981 | −1.8 | 0.718 | 0.731 | −1.8 | 0.740 | 0.988 |
| $C_3H_8$ | 90 | 80 | 789 | 162 | 37 | 995 | 993 | −0.2 | 0.783 | 0.796 | −0.2 | 0.791 | 1.006 |
| iso-$C_4H_{10}$ | 90 | 80 | 726 | 219 | 61 | 1002 | 1040 | 3.8 | 0.725 | 0.688 | 3.6 | 0.704 | 0.992 |

TABLE 3

| Component | Extraction condition | | Extracted-gas concentration $X_n$ (μL/L) | | | Adjusted concentration [μL/L] | Calculated concentration [μL/L] | Error (concentration) [%] | Actual extraction rate [—] | Extraction rate R1 [—] | Error (extraction) [%] | Extraction rate R2 [—] | R1/R2 [—] |
|---|---|---|---|---|---|---|---|---|---|---|---|---|---|
| | Time (second) | Temperature (° C.) | 1st time $X_1$ | 2nd time $X_2$ | 3rd time $X_3$ | | | | | | | | |
| $CH_4$ | 45 | 100 | 859 | 39 | 20 | 999 | 971 | −2.8 | 0.860 | 0.885 | −2.9 | 0.876 | 1.010 |
| $C_2H_4$ | 45 | 100 | 828 | 136 | 29 | 995 | 991 | −0.4 | 0.832 | 0.836 | −0.4 | 0.829 | 1.008 |
| $C_2H_2$ | 45 | 100 | 832 | 145 | 35 | 999 | 1008 | 0.9 | 0.833 | 0.826 | 0.9 | 0.816 | 1.012 |
| $C_3H_8$ | 45 | 100 | 734 | 221 | 59 | 995 | 1050 | 5.5 | 0.738 | 0.699 | 5.3 | 0.707 | 0.989 |
| iso-$C_4H_{10}$ | 45 | 100 | 864 | 258 | 98 | 1002 | 1086 | 8.4 | 0.663 | 0.611 | 7.7 | 0.614 | 0.996 |

As shown in Tables 1 to 3, regardless of the extraction temperature conditions, the extraction rate ratio R1/R2 is in the range of 0.90 to 1.01 as well as the error (concentration) is 10% or less in absolute value. Therefore, it is proved that the in-oil gas concentration can be measured with high accuracy. Thus, it is proved that the in-oil gas concentration can be measured with high accuracy without preparing a reference sample by using the in-oil gas concentration measuring system and the measuring method of the present invention.

REFERENCE SIGNS LIST

1 Syringe
2 Insulating oil sample
3 Sample inlet
4 Extractor
5 Gas passage
6 Branch pipe
7 Joint
8 Oil trap
9 Gas chromatograph
10 In-oil gas concentration measuring system
11 Gas extracting means
12 Component detecting means
13 Extractor
14 Electric six-direction switching cock (a)
15 Sample holding container
16 Measuring means (measuring tube)
17 Feed pump
18 Discharge preventing means
19 Heating means
20 Waste container
21 Detecting unit
22 Arithmetic unit
23 Flow line switching means (electric six-direction switching cock (b))
24 Separator 25 Component detector
26 Flow regulating valve
27 Processing unit
28 Storage unit
29 Input means
30 Display means
31 Extracted-gas concentration calculating section
32 In-oil gas concentration calculating section
33 Detected data storing section
34 Extracted-gas concentration storing section
35 In-oil gas concentration storing section
36 Waste container
L1 Line
P1 to P10 Passage
V1 to V3 Solenoid valve

The invention claimed is:

1. An in-oil gas concentration measuring system comprising:
    gas extracting means for extracting an in-oil gas from an insulating oil sample;
    component detecting means for detecting gas components of the in-oil gas extracted by the gas extracting means;
    extracted-gas concentration calculating means for calculating extracted-gas concentrations of the gas components being detected, based on data detected by the component detecting means;
    extracted-gas concentration storing means for storing information on the extracted-gas concentrations calculated by the extracted-gas concentration calculating means as a result of two or more extractions performed by the gas extracting means, the information being stored in each of the extractions; and
    in-oil gas concentration calculating means for calculating in-oil gas concentrations of the gas components based on the extracted-gas concentrations stored in the extracted-gas concentration storing means,
    wherein the in-oil gas concentration calculating means calculates an in-oil gas concentration (Q) by using the following equation (1), where Q denotes an in-oil gas concentration to be calculated, R denotes an extraction rate of an in-oil gas, and $X_n$ denotes an extracted-gas concentration at n-th time extracted from the extracted-gas concentration storing means $$X_n = R\left(Q - \sum_{k=1}^{n} X_{k-1}\right) (n = 1, 2, \text{ and so on}, X_0 = 0). \quad (1)$$

2. The in-oil gas concentration measuring system according to claim 1, wherein the component detecting means is provided with flow line switching means for controlling opening and closing of a gas flow line for supplying the in-oil gas extracted by the gas extracting means to the component detecting means.

3. The in-oil concentration measuring system according to claim 1, wherein the gas extracting means is provided with discharge preventing means for the insulating oil sample.

4. The in-oil gas concentration measuring system according to any one of claims 1 to 3, wherein the gas extracting means is composed of an in-oil gas extracting apparatus having measuring means for measuring the insulating oil sample.

5. An in-oil gas concentration measuring method comprising:
    providing gas extracting means for extracting an in-oil gas from an insulating oil sample, component detecting means for detecting gas components of the in-oil gas extracted by the gas extracting means, extracted-gas concentration calculating means for calculating extracted-gas concentrations of the gas components being detected, based on data detected by the component detecting means, extracted-gas concentration storing means for storing information on the extracted-gas concentrations calculated by the extracted-gas concentration calculating means, and in-oil gas concentration calculating means for calculating in-oil gas concentrations of the gas components based on the extracted-gas concentrations stored in the extracted-gas concentration storing means;
    performing a sequence of steps twice or more, the steps including extracting an in-oil gas by the gas extracting means, detecting gas components of the in-oil gas by the component detecting means, calculating gas concentrations of the gas components being detected, by the extracted-gas concentration calculating means, and storing information on the extracted-gas concentrations by the extracted-gas concentration storing means; and
    calculating an in-oil gas concentration (Q) by the in-oil gas concentration calculating means by using the following equation (1), where Q denotes an in-oil gas concentration to be calculated, R denotes an extraction rate of an in-oil gas, and $X_n$ denotes an extracted-gas concentration at n-th time extracted from the extracted-gas concentration storing means $$X_n = R\left(Q - \sum_{k=1}^{n} X_{k-1}\right) (n = 1, 2, \text{ and so on}, X_0 = 0). \quad (1)$$

6. The in-oil concentration measuring system according to claim 2, wherein the gas extracting means is provided with discharge preventing means for the insulating oil sample.

* * * * *